(12) United States Patent
Hopping et al.

(10) Patent No.: US 8,449,495 B2
(45) Date of Patent: May 28, 2013

(54) DIALYSIS SYSTEM HAVING AUTOMATED EFFLUENT SAMPLING AND PERITONEAL EQUILIBRATION TEST

(75) Inventors: Peter Hopping, Tampa, FL (US); Steve J. Lindo, Chicago, IL (US); Meir Dahan, Lincolnwood, IL (US); Robert W. Childers, New Port Richey, FL (US)

(73) Assignees: Baxter Healthcare Inc., Deerfield, IL (US); Bacter Healthcare S.A., Glattpark (Opfikon) (CH)

( * ) Notice: Subject to any disclaimer, the term of this patent is extended or adjusted under 35 U.S.C. 154(b) by 469 days.

(21) Appl. No.: 12/128,385

(22) Filed: May 28, 2008

(65) Prior Publication Data

US 2009/0299272 A1 Dec. 3, 2009

(51) Int. Cl.
*A61M 1/00* (2006.01)

(52) U.S. Cl.
USPC ............... 604/29; 604/28; 604/131; 604/189; 604/318; 604/533

(58) Field of Classification Search
USPC .................. 604/28, 29, 131, 189, 533, 318
See application file for complete search history.

(56) References Cited

U.S. PATENT DOCUMENTS

| | | | |
|---|---|---|---|
| 4,192,748 A | 3/1980 | Hyden | |
| 4,244,787 A | 1/1981 | Klein et al. | |
| 4,508,622 A | 4/1985 | Polaschegg et al. | |
| 5,141,327 A | 8/1992 | Shiobara | |
| 5,360,013 A * | 11/1994 | Gilbert | 600/584 |
| 5,442,969 A | 8/1995 | Troutner et al. | |
| 5,518,623 A | 5/1996 | Keshaviah et al. | |
| 5,567,320 A | 10/1996 | Goux et al. | |
| 5,725,773 A * | 3/1998 | Polaschegg | 210/636 |
| 5,733,442 A | 3/1998 | Shukla | |
| 5,744,031 A | 4/1998 | Bene | |
| 5,788,846 A | 8/1998 | Sternby | |
| 5,954,951 A | 9/1999 | Nuccio | |
| 6,205,869 B1 * | 3/2001 | Schadt et al. | 73/863.71 |
| 6,247,840 B1 | 6/2001 | Gaffar | |
| 7,115,113 B2 * | 10/2006 | Evans et al. | 604/189 |
| 7,303,541 B2 * | 12/2007 | Hamada et al. | 604/29 |
| 2001/0040127 A1 | 11/2001 | Donig et al. | |

(Continued)

FOREIGN PATENT DOCUMENTS

| | | |
|---|---|---|
| EP | 0 621 046 | 10/1994 |
| EP | 0 711 569 | 5/1996 |

(Continued)

OTHER PUBLICATIONS

Vonesh EF, Story K, O'Neill WT for The PD Adequest International Study Group. Petit Dial Int 1999; 19:556-571.

(Continued)

*Primary Examiner* — Bhisma Mehta
*Assistant Examiner* — Larry R Wilson
(74) *Attorney, Agent, or Firm* — K&L Gates LLP

(57) ABSTRACT

A dialysis system includes at least one dialysis fluid pump actuator, a disposable cassette including at least one pump chamber operable with the at least one pump actuator, the disposable cassette further including a plurality of fluid ports configured to be connected fluidly to a plurality of fluid containers, and a processor programmed to cause the at least one pump actuator to operate the at least one pumping chamber to selectively move effluent dialysis fluid to a drain container or to a sample container.

28 Claims, 12 Drawing Sheets

U.S. PATENT DOCUMENTS

| | | | |
|---|---|---|---|
| 2005/0008999 | A1 | 1/2005 | Blossom et al. |
| 2007/0112297 | A1* | 5/2007 | Plahey et al. ............ 604/28 |
| 2007/0179435 | A1* | 8/2007 | Braig et al. ............ 604/66 |

FOREIGN PATENT DOCUMENTS

| | | |
|---|---|---|
| EP | 0 815 882 | 1/1998 |
| EP | 0815882 A2 | 1/1998 |
| EP | 1 195 171 | 4/2002 |
| FR | 2 696 644 | 4/1994 |
| JP | 62-9444 | 1/1987 |
| JP | 11-319075 | 11/1999 |
| WO | 82/04127 | 11/1982 |
| WO | 96/33753 | 10/1996 |

OTHER PUBLICATIONS

Heimburger O, Waniewski J. Ultrafiltration Failure in Peritoneal Dialysis Patients. Petit Dial Int 2004; 24:506-508.

Mujais S, Nolph K, Gokal R, et al. Evaluation and Management of Ultrafiltration Problems in Peritoneal Dialysis. Petit Dial Int 2000; 20:S4, S5-21.

Abu-Alfa Ak, Burkhard J, Piraino b, Pulliam J, Mujais S. Approach to Fluid Management in Peritoneal Dialysis: A Practical Algorithm. Kidney Int 2002; 62:S81 S8-S16.

La Milia V, Di Filippo, Crepaldi M et al. Mini-Peritoneal Equilibration Test: A Simple and Fast Method to Assess Free Water and Small Solute Transport Across the Peritoneal Membrane. Kidney Int 2005; 68:840-846.

Blake P. Individualized Prescription of Peritoneal Dialysis Therapy. Peritoneal Dialysis International, vol. 19, Supp. 2, 1999.

Brunkhorst R. Individualized PD Prescription: APD Versus CAPD. Peritoneal Dialysis International, vol. 25, Supp. 3, 2005.

Rippe B. et al. Computer Simulation of Peritoneal Fluid Transport in CAPD. Kidney International, vol. 40 (1991), pp. 315-325.

Waniewski J. Mathematical Modeling of Fluid and Solute Transport in Hemodialysis and Peritoneal Dialysis. J. of Membrane Science 274 (2006), 24-37.

Vonesh E. et al. Kinetic Modeling as a Prescription Aid in Peritoneal Dialysis. Blood Purif 1991; 9: 246-270.

Prowant BF, Schmidt LM. The Peritoneal Equilibration Test: A Nursing Discussion. *ANNA J.* 1991; 18:361-366.

Schmidt LM, Prowant BF. How to do a Peritoneal Equilibration Test. *ANNA J.* 1991; 18: 368-370.

Twardowski ZJ, Nolph KD, Khanna R, et al. Peritoneal Equilibration Test. *Perit Dial Bull*. 1987; 7:138-147.

Twardowski ZJ, Clinical Value of Standardized Equilibration Tests in CAPD patients. *Blood. Purif.* 1989; 7:95-108.

Twardowski ZJ, Prowant BF, Moore HL, Lou LC, White E, Farris K. Short Peritoneal Equilibration Test: Impact of Preceding Dwell Time. *Adv Perit Dial*. 2003: 19:53-58.

Lilaj T, Dittrich E, Puttinger H, et al. A Preceding Exchange with Polyglucose Versus Glucose Solution Modifies Peritoneal Equilibration Test Results. *Am J Kidney Dis*. 2001; 38:118-126.

International Search Report and Written Opinion for International Application No. PCT/US2009/045169 dated Dec. 12, 2009.

Japanese Office Action issued Aug. 16, 2012, corresponding to Japanese Appln. No. 2011-511755.

\* cited by examiner

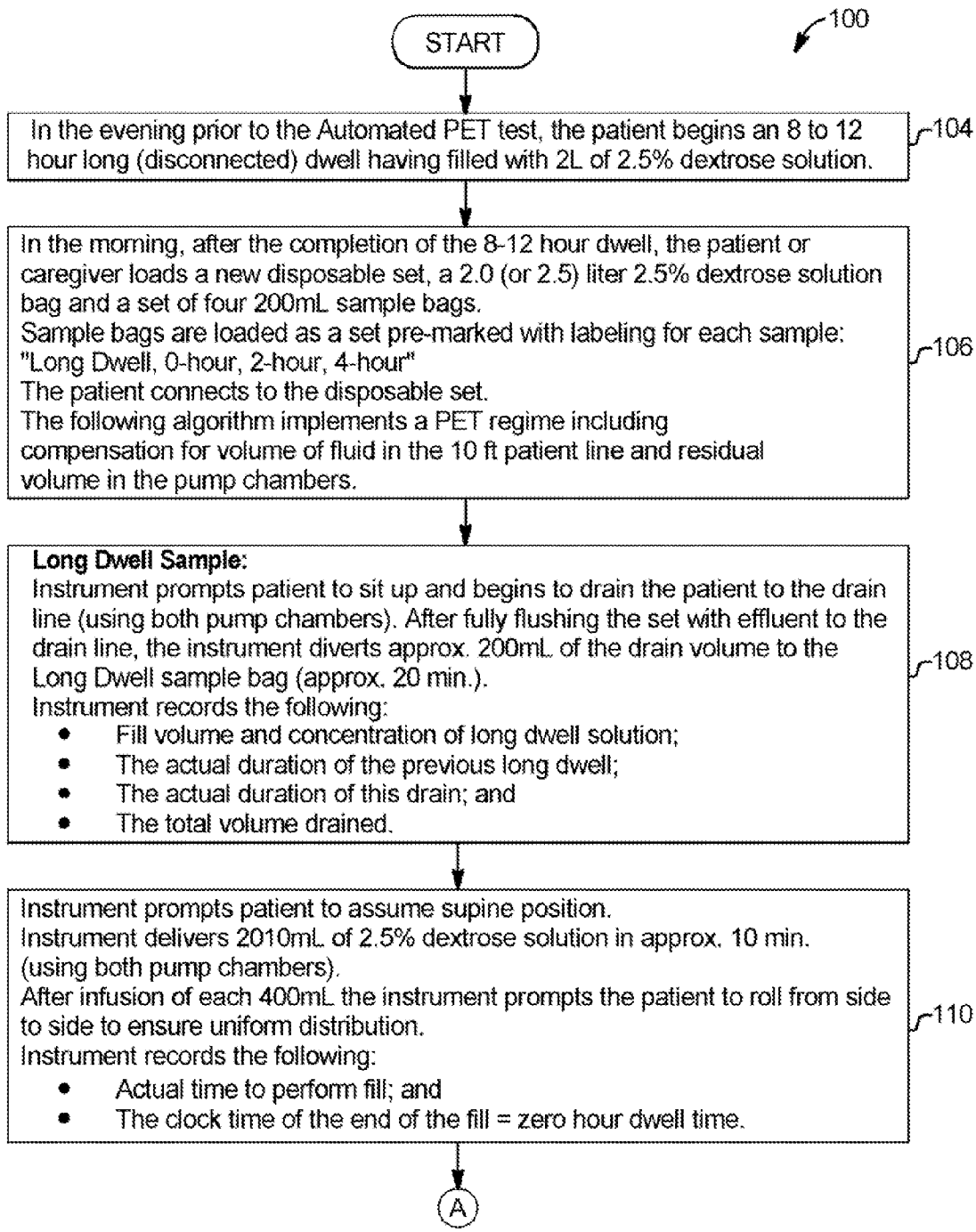

FIG. 9B

0-hour sample:
At the end of this fill, the instrument will drain approx. 40mL (volume of patient line) to the drain line (to flush the patient line) using pump chamber A. The instrument will then drain 200mL (of the fluid that was just infused) into the sample bag labeled 0-hour dwell using pump chamber B. Then 190 mL is pulled back from the same sample bag using pump chamber B and re-infused into the patient leaving10mL for a sample. Then 40mL of fresh dialysate is pumped to the patient using pump chamber A (this fresh solution only enters the patient line pushing the solution that came out of the patient back in).
Patient may now disconnect or remain connected until the next sample. ⎯112

2-hour sample and 2-hour blood sample:
Allow the solution to continue to dwell in the peritoneum until 2 hours after zero-hour dwell time. Patient reconnects prior to the end of the 2 hours.
At the end of the 2 hours, instrument will drain 40mL to the drain line to flush the patient line using pump chamber A.
Next the instrument drains 200mL from the patient into the sample bag labeled 2-hour dwell using pump chamber B.
Then 190mL is pulled back from the same sample bag and re-infused into the patient using pump chamber B, leaving 10mL for a sample. Finally, 40mL of fresh dialysate is pumped to the patient using pump chamber A (this solution only enters the patient line pushing the solution that came out of the patient back in).
Instrument records the following:
- Time of sample

*At this time a 2-hour blood sample is also taken.*
Instrument prompts for blood serum sample to be taken. ⎯114

4-hour sample:
Allow the solution to continue to dwell in the peritoneum until 4 hours after the zero-hour dwell time. Patient must reconnect prior to the end of the 4 hours.
At the end of the 4 hours, instrument prompts patient to assume sitting position and begins to drain the patient to the drain line (using both chambers). After fully flushing the set with effluent to the drain line, the instrument diverts approx. 200mL of the drain volume to the sample bag labeled 4-hour dwell and then completes the drain to the drain line (Approx. 20 min.).
The instrument records the following:
- Time of sample; and
- The total drained volume This concludes the four PET samples.
Patient may now disconnect. ⎯116

( END )⎯118

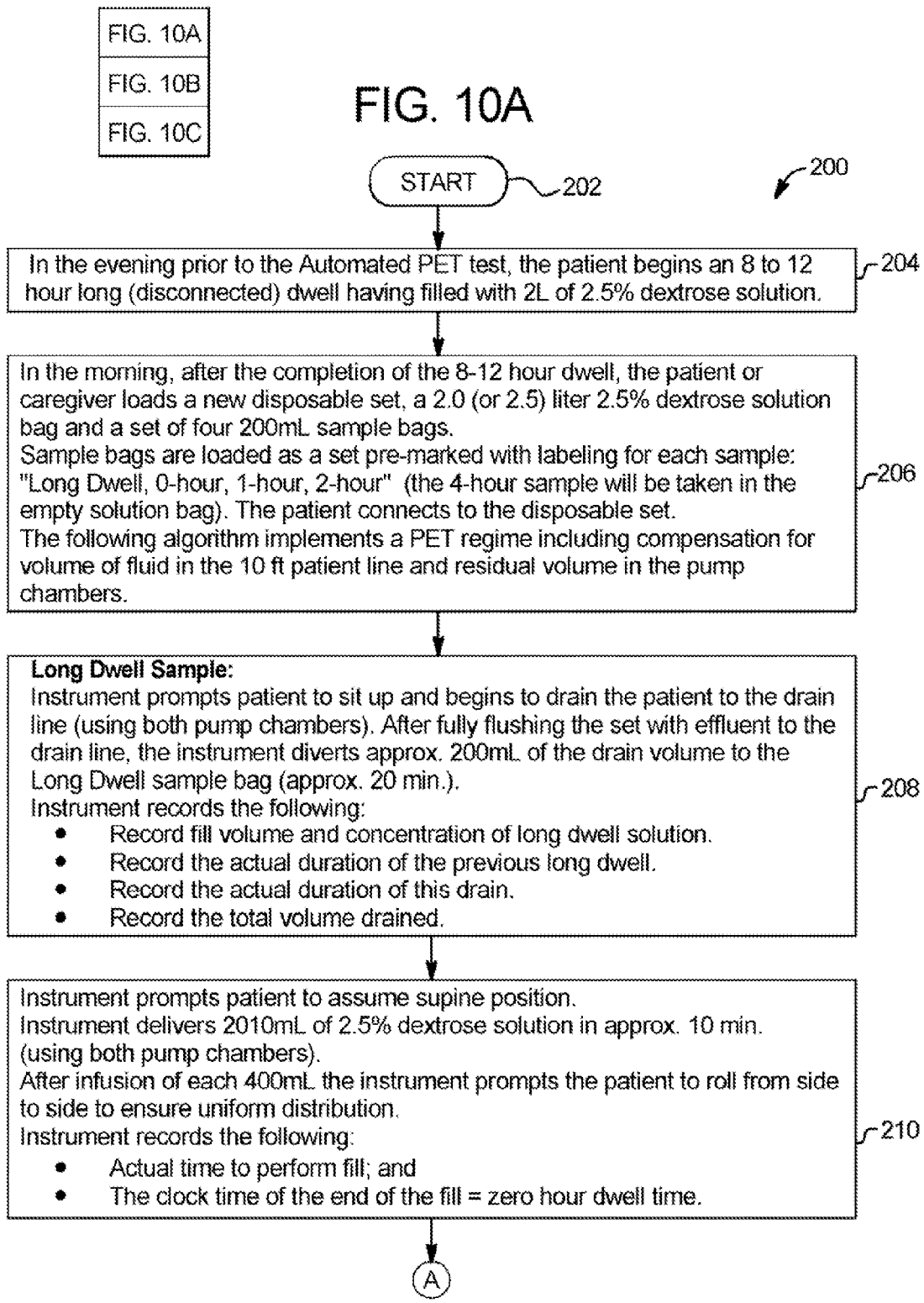

FIG. 10B (A)

0-hour sample:
At the end of this fill, the instrument will drain approx. 40mL (volume of patient line) to the drain line (to flush the patient line) using pump chamber A. The Instrument will then drain 200mL (of the fluid that was just infused) into the sample bag labeled 0-hour dwell using pump chamber B. Then 190 mL is pulled back from the same sample bag using pump chamber B and re-infused into the patient leaving10mL for a sample. Then 40mL of fresh dialysate is pumped to the patient using pump chamber A (this fresh solution only enters the patient line pushing the solution that came out of the patient back in).
Patient may now disconnect or remain connected until the next sample. — 212

1-hour sample:
Allow the solution to continue to dwell in the peritoneum until 1 hour after zero-hour dwell time.
Patient reconnects prior to the end of the 1 hour.
At the end of 1 hour, instrument will drain 40mL to the drain line to flush the patient line using pump chamber A.
Next the instrument drains 200mL from the patient into the sample bag labeled 2-hour dwell using pump chamber B.
Then 190mL is pulled back from the same sample bag and re-infused into the patient using pump chamber B, leaving 10mL for a sample. Finally, 40mL of fresh dialysate is pumped to the patient using pump chamber A (this solution only enters the patient line pushing the solution that came out of the patient back in).
Instrument records the following:
- Time of sample

2-hour sample and 2-hour blood sample:
Allow the solution to continue to dwell in the peritoneum until 2 hours after zero-hour dwell time. Patient reconnects prior to the end of the 2 hours.
At the end of the 2 hours, instrument will drain 40mL to the drain line to flush the patient line using pump chamber A.
Next the instrument drains 200mL from the patient into the sample bag labeled 2-hour dwell using pump chamber B.
Then 190mL is pulled back from the same sample bag and re-infused into the patient using pump chamber B, leaving 10mL for a sample. Finally, 40mL of fresh dialysate is pumped to the patient using pump chamber A (this solution only enters the patient line pushing the solution that came out of the patient back in).
Instrument records the following:
- Time of sample

*At this time a 2-hour blood sample is also taken.*
Instrument prompts for blood serum sample to be taken. ⟋216

4-hour sample:
Allow the solution to continue to dwell in the peritoneum until 4 hours after the zero-hour dwell time. During the dwell, after the 2-hour sample is complete, any remaining supply volume is emptied to drain (using both chambers).
Patient reconnects prior to the end of the 4 hours.
At the end of the 4 hours, instrument prompts patient to assume sitting position and begins to drain the patient to the drain line (using both chambers). After fully flushing the set with effluent to the drain line, the instrument sequentially diverts 500mL to the empty supply bag and then empties that 500mL effluent in the supply bag to drain and repeats this until the patient is empty, leaving a small volume in the supply bag. This will successively dilute any remaining solution in the supply bag until it is of no consequence.
The 4-hour sample is taken from the supply bag containing the last portion of solution drained. A 10ml sample is taken by syringe from the supply bag or the supply bag is sent as is along with the four sample bags.
The instrument records the following:
- Time of sample; and
- The total drained volume This concludes the five modified PET samples.
Patient may now disconnect. ⟋218

END ⟋220

DIALYSIS SYSTEM HAVING AUTOMATED EFFLUENT SAMPLING AND PERITONEAL EQUILIBRATION TEST

BACKGROUND

The present disclosure relates to dialysis and in particular to effluent sampling test for peritoneal dialysis.

Prescribing a dose of dialysis fluid for peritoneal dialysis ("PD") patients is based typically on results from a peritoneal equilibration test ("PET") developed originally by Dr. Zbylut J. Twardoski. The PET can be performed on a routine basis or when a nurse or clinician requests that a PET be performed. In current practice, patients have to travel to a dialysis center, so that a trained nurse or clinician can perform the PET in a manually intensive operation. A typical PET regime requires the nurse or clinician to take numerous solution samples over the course of approximately four to five hours.

If the nurse or clinician requests an effluent sample (for peritonitis testing, for a PET or for any desired reason) from a first drain, patients using known PD cyclers have to remain awake and collect the effluent sample at the proper sequence in therapy manually. The patient or clinician also has to open and close clamps manually at appropriate times during therapy to prevent contamination of the effluent sample.

Alternatively, if the clinician requests that an effluent sample (for adequacy testing or for any desired reason) be taken from the patient's total drain solution (all drain cycles combined), the patient has to perform an extra step at the end of therapy. This extra step requires the patient to pour fluid from a relatively large drain bag or container (e.g., fifteen liters) into a smaller effluent sample bag. The effluent sample bag or container may be connected to a Y in the drain line so that sterility is not an issue. Sometimes however the drain container is not connected to the drain line, meaning that the patient could spill the effluent sample when attempting to pour it into the separate container. Further, pouring fluid into a separate container can lead to contamination.

Still further, patients are sometimes requested to bring their entire effluent sample bag to a dialysis clinic to ensure an adequate sample volume is taken. This bag is heavy and cumbersome. Also, a disadvantage of bringing the entire drain bag is that the drain bag is typically diluted with several hundred milliliters of fresh dialysis solution due to priming and flushing of a disposable set at the beginning of therapy. The addition of the fresh dialysis fluid to the overall drain container can skew the effluent sampling results.

Accordingly, an improved apparatus and method for performing a PET and for effluent sampling generally is needed for PD.

SUMMARY

The present disclosure relates generally to an automated system for performing a peritoneal equilibration test ("PET") and for taking effluent samples for any desired reason. The automated system removes the manual and memory burdens placed on the patient to a large extent. The system collects effluent samples automatically from either a particular drain cycle or from an aggregate of drained solution, in one embodiment without the need for the patient to perform an extra clamping or pouring step. The system in one embodiment provides effluent sampling bags that connect to a disposable pumping component, which operate with a dialysis fluid pumping instrument. The effluent bags in one embodiment have an identifier, such as a radio frequency identifier, or optical bar code, embedded into the connector of the bag, which the machine reads to know that the bag is an effluent sample bag as opposed to a different type of bag, such as a supply or drain bag. The effluent sample bag can be provided in varying sizes to accommodate any volume that the clinician requires. The effluent sample bags in one embodiment are also printed with a series of progressively lighter text on one side of the bag. When filled with effluent and placed on a white background, the text becomes an indicator to the patient of cloudy effluent, which can be an early sign of peritonitis.

The dialysis instrument ensures that the sample is representative of the entire drain volume when collecting a sample of the total effluent drained from the patient. To do so, the system in one embodiment ratiometrically delivers part of the drain volume to the drain bag and part to the sample bag. For example, to obtain an approximate one liter sample of drained solution and assuming the patient's total fill volume is ten liters, the instrument can be configured to perform nine drain pump strokes to the drain bag and one drain pump stroke to the sample bag. The ratiometric pumping continues to the end of therapy, providing a sample that is representative over the entire drain.

The effluent sampling system in an alternative embodiment is programmed to take an effluent sample from a particular drain cycle rather than from each of the drain cycles. For example, a dialysis therapy could consist of three drains including an initial drain. The sample could be taken from only the initial drain, only the second drain or only the final drain as desired. The system caps the effluent bag line connector automatically when the sample is completed. Such automatic capping eliminates the need for a separate manual clamp and a separate manual step that the patient would otherwise have to take, although the system can operate without automatic capping.

The above-described effluent sampling system produces a single effluent sampling bag. The above-mentioned PET typically requires that multiple samples be taken at different time intervals during a treatment. The effluent sampling system of the present disclosure in an alternative embodiment is accordingly configured to perform a PET automatically, yielding multiple sample bags, with samples taken at different times over the course of a sample treatment. The system performs all of the effluent sample collections automatically, reducing the time burden on the patient or clinician. It is contemplated in one embodiment to perform the PET automatically in a center because the PET typically requires that a blood sample also be taken. Here, a nurse or clinician at the center takes the blood sample. It is also contemplated however to perform the automated PET at home, assuming the patient is equipped to take the blood sample or is with a nurse or caregiver at home who can take the blood sample. In any case, the patient or clinician likely only has to take a single blood serum sample, for example at the two-hour effluent sample point. The automated PET system in one embodiment is configured to prompt the patient or clinician to take such blood serum sample.

The dialysis system is provided with a data storage capability, which captures and records all relevant data generated during the PET on a patient data card. The data card is then used to transfer the information to clinical software for later processing with the lab analysis of the effluent sample and serum sample data.

It is accordingly one advantage of the present disclosure to provide a sterile effluent sampling system that eliminates a currently existing Y connector on the drain line for sampling.

It is another advantage of the present disclosure to provide a dialysis system capable of effluent sampling that eliminates the need for a larger, e.g., fifteen liter drain bag, which is costly to the customer and is not needed in the present system because effluent fluid not used for the sample can be delivered directly to a drain.

Still another advantage of the present disclosure is to provide an effluent sampling system that provides a more accurate sample by pumping the initial priming and flushing volume to the drain bag or to house drain but in either case not to the sample bag.

It is a further advantage of the present disclosure to provide an automated peritoneal equilibration test ("PET").

It is yet another advantage of the present disclosure to reduce burden on clinicians at dialysis centers.

Additional features and advantages are described herein, and will be apparent from, the following Detailed Description and the figures.

BRIEF DESCRIPTION OF THE FIGURES

FIG. 9, which includes FIGS. 9A and 9B, is a schematic flow diagram illustrating one sequence of operation for the automated PET of the present disclosure.

FIG. 10, which includes FIGS. 10A, 10B and 10C, is a schematic flow diagram illustrating another sequence of operation for the automated PET of the present disclosure.

DETAILED DESCRIPTION

Figure 1:
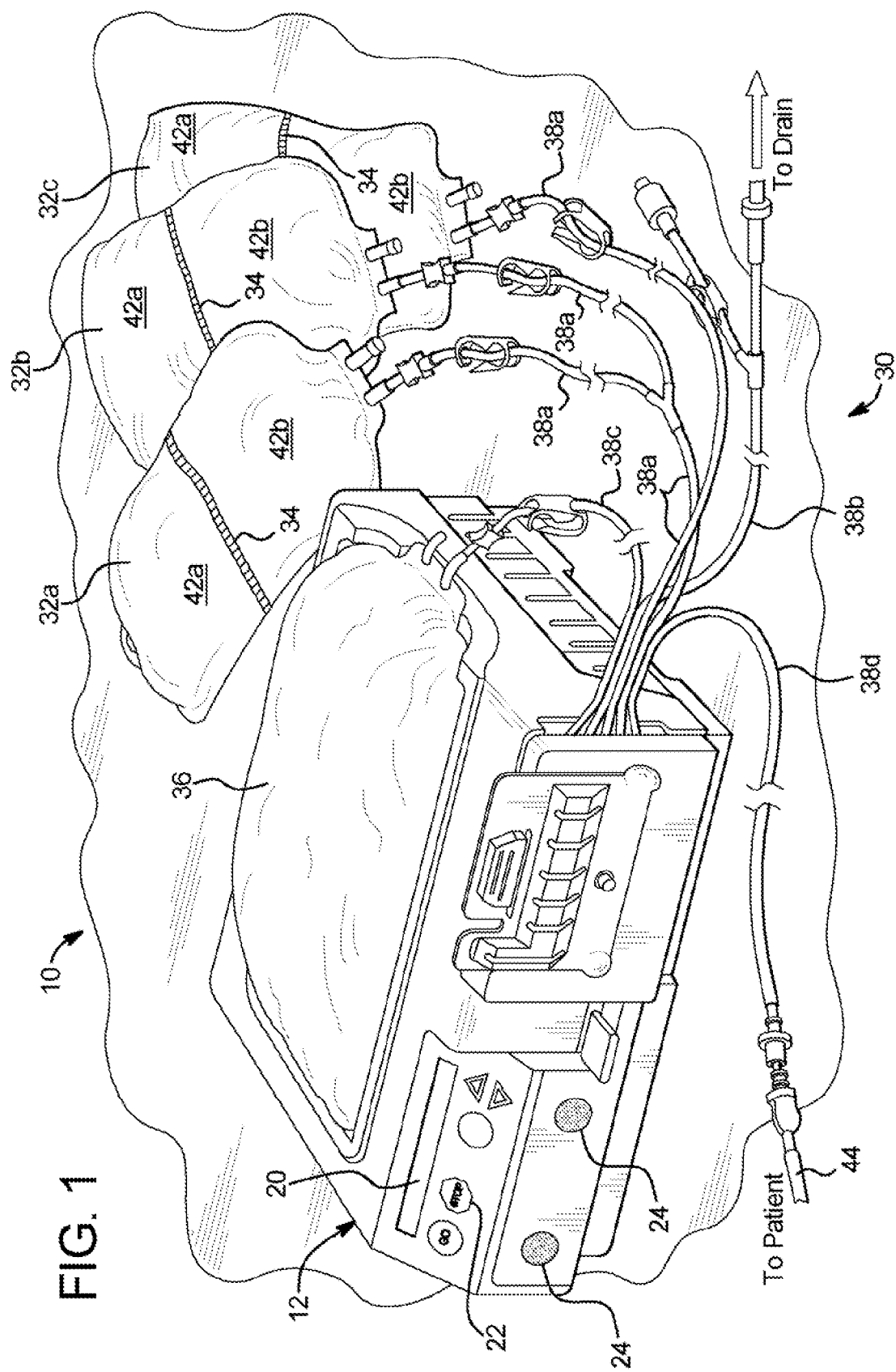
FIG. 1 is a perspective view of one embodiment of a dialysis system programmed to run the automated effluent sampling and peritoneal equilibration test ("PET") of the present disclosure.
Figure 2:
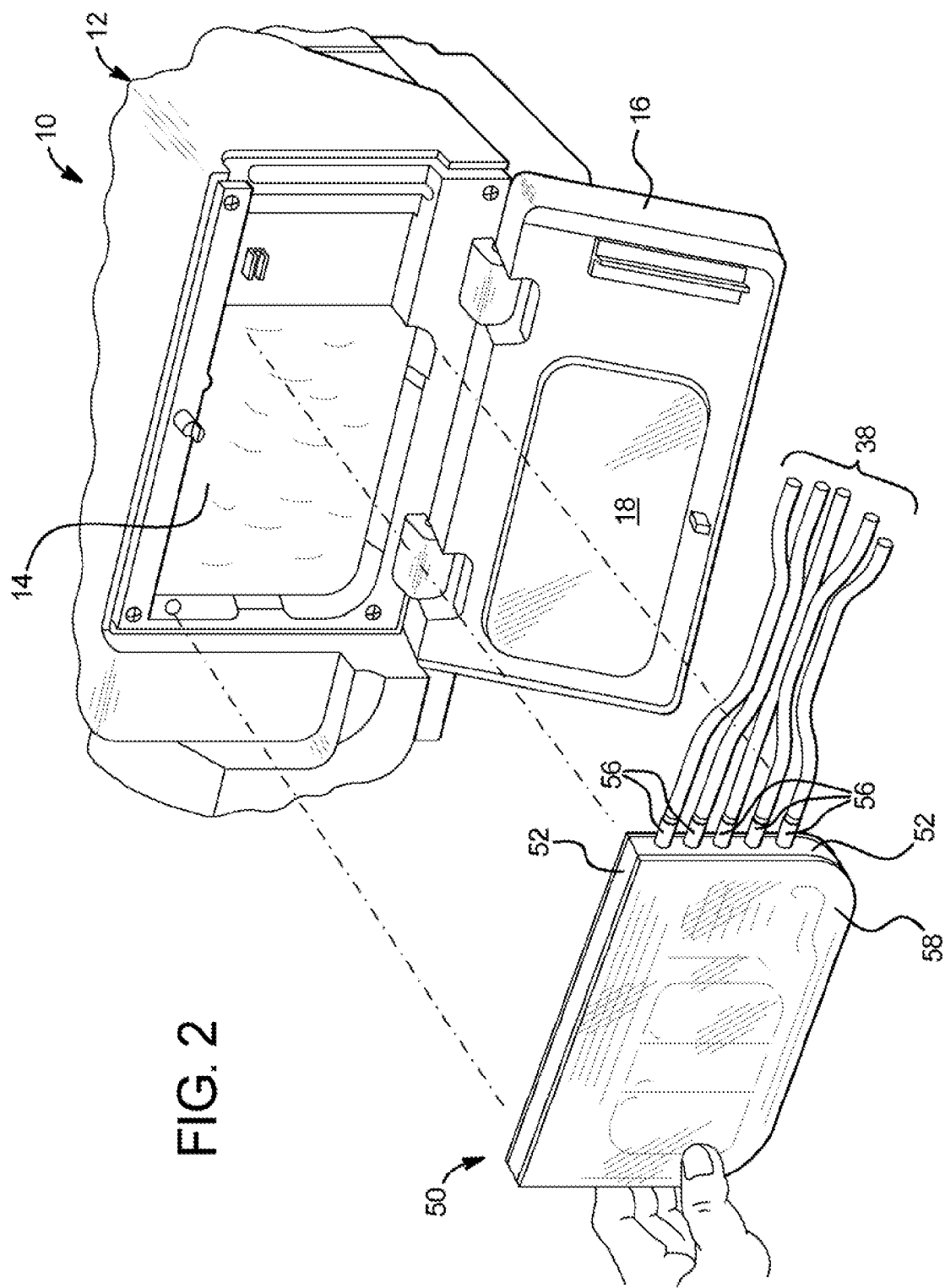
FIG. 2 is a perspective view of the system of FIG. 1 highlighting the operation of the disposable cassette with the system.

Referring now to the drawings and in particular to FIGS. 1 to 2, a renal failure therapy system 10 is provided. System 10 is applicable generally to any type of renal failure therapy system, such as peritoneal dialysis ("PD"), hemodialysis ("HD"), hemofiltration ("HF"), hemodiafiltration ("HDF") and continuous renal replacement therapy ("CRRT"). The automated sampling system described below could also be used outside of the renal field, such as for medication delivery in general and for blood processing. For ease of illustration, however, system 10 is described in general as a dialysis system, and in one particularly well-suited application as a PD system.

System 10 in the illustrated embodiment includes a dialysis instrument 12. Dialysis instrument 12 is configured for whichever type of renal failure therapy system is used. Dialysis instrument 12 includes a central processing unit ("CPU") and a plurality of controllers (e.g., safety, valve, heater, pump, video and audio (e.g., voice guidance) controllers) operable with the CPU. The CPU operates with a graphical user-machine interface ("GUI"), e.g., via the video controller, which includes a video monitor 20 and one or more type of input device 22, such as a touch screen or electromechanical input device (e.g., membrane switch).

The CPU and video controller in cooperation with video monitor 20 provide automated sampling and peritoneal equilibration test ("PET") instructions visually via characters/graphics to the patient or caregiver. For example, characters/graphics can be displayed to provide instructions regarding use of a sample container 70 (FIGS. 3 to 6) with system 10. Additionally or alternatively, The CPU and voice guidance controller in cooperation with speakers 24 provide automated sampling and PET instructions via voice guidance to the patient or caregiver. For example, voice guidance can be given to provide instructions regarding the use of a sample container 70 with system 10.

As seen in FIG. 1, dialysis instrument 12 accepts and operates with a disposable apparatus 30. Disposable apparatus 30 includes one or more supply bag 32a to 32c (referred to herein collectively as supply bags 32 or individually, generally as supply bag 32), shown here as dual-chamber supply bags separating two fluids via a peel or frangible seal 34. Disposable set 30 also includes a drain bag (not illustrated), a warmer bag 36, bag tubes 38a to 38d (referred to herein collectively as tubing or tubes 38 or individually, generally as tube 38) and a disposable pumping/valve cassette 50 (FIG. 2).

Depending on the type and structure of the renal failure therapy system 10, one or more of the items of disposable apparatus 30 may not be needed. For example, system 10 can pump spent fluid to a house drain, such as a bathtub, a toilet or sink, instead of to a drain bag. System 10 can also include an inline heater, in which case warmer bag 36 is not needed.

While three supply bags 32 are shown, system 10 can employ any suitable number of supply bags. Supply bags 32 are shown having multiple chambers 42a and 42b, separated by a frangible seal 34, which hold different solutions depending on the type of therapy employed. For example, chambers 42a and 42b can hold buffer and glucose for PD or acetate and bicarbonate solution for HD. Supply bags 32 are alternatively single chamber bags, which hold a single premixed solution, such as premixed PD or HD dialysate.

As seen in FIGS. 1 and 2, a disposable cassette 50 connects to supply bags 32, drain bag and warmer bag 36 via tubes 38a, 38b and 38c, respectively. Tube 38d runs from cassette 50 to a patient connection 44. Cassette 50 in one embodiment includes a rigid structure having rigid outer walls 52, a base wall from which inner pump chambers (60 as shown below), valve chambers (62 as shown below) and inner fluid pathways extend, rigid fluid ports 56 (referring collectively to ports 56a to 56g shown below) that connect sealingly to tubing 38, and a pair of flexible membranes or sheets 58 sealed to outer rigid walls 52 and possibly, additionally to inner rigid walls. Tubing 38 can be fixed to port 56, such that bags 52 are spiked for fluid connection. Alternatively, tubing 58 is fixed to bags 32 and ports 56 are spiked for fluid connection.

Instrument 12 can actuate the pump and valve chambers of cassette 50 pneumatically, mechanically or both. The illustrated embodiment uses pneumatic actuation. The HomeChoice® APD system marketed by the eventual assignee of the present disclosure, which could operate or be made operable with cassette 50, uses a pneumatic system described in U.S. Pat. No. 5,350,357 ("The '357 Patent"), the entire contents of which are incorporated herein by reference. In the illustrated embodiment, instrument 12 includes a membrane gasket 14, which creates different sealed areas with cassette sheeting 58 at each of the pump and valve chambers of cassette 50. Membrane gasket 14 moves with the cassette sheeting 58 in those areas to either open/close a valve chamber or pump fluid through a pump chamber. An interface plate is located behind membrane gasket 14 and forms part of each of a pair of fixed volume pump chambers in combination with the pump chambers (actually pump chamber portion) of cassette 50 discussed below.

Instrument 12 in the illustrated embodiment includes a door 16, which closes against cassette 50. Door 16 includes a press plate 18, which can be operated mechanically (e.g., via the closing of the door) and/or pneumatically (e.g., via an inflatable bladder located in the door behind the press plate). Pressing plate 18 against cassette 50 in turn presses cassette 50 against a pumping membrane 14 that cooperates with the sheeting 58 of cassette 50 to pump fluid and open and close valves.

The cassette interface plate (not seen) is located behind membrane gasket 14. The cassette interface plate is configured to apply positive or negative pressure to the cooperating membrane gasket 14 and cassette sheeting 58 at the different valve and pump areas. For example, positive pressure is applied to membrane 14/sheeting 58 at an area of the membrane 14 sheeting 58 located within the internal walls of cassette 50 defining the pump chambers to push fluid out of the pump chambers. Negative pressure is applied to membrane 14/sheeting 58 at that same area to pull fluid into the pump chambers. Positive pressure is applied to membrane 14/sheeting 58 at an area of the sheeting within the internal walls of cassette 50 defining the valve chambers to close outlet ports of the valve chambers. Negative pressure is applied to membrane gasket 14/sheeting 58 at those same areas of membrane gasket 14/sheeting 58 to open an outlet of the valve chambers.

U.S. Pat. No. 6,814,547 ("the '547 patent") assigned to the assignee of the present disclosure, discloses a pumping mechanism in connection with FIGS. 17A and 17B, incorporated herein by reference, which uses a combination of pneumatic and mechanical actuation. FIGS. 15, 16A and 16B of the '547 Patent, incorporated herein by reference, teach the use of mechanically actuated valves. Either or both the '547 pumping mechanism or valves could be used alternatively with system 10.

Figure 3:
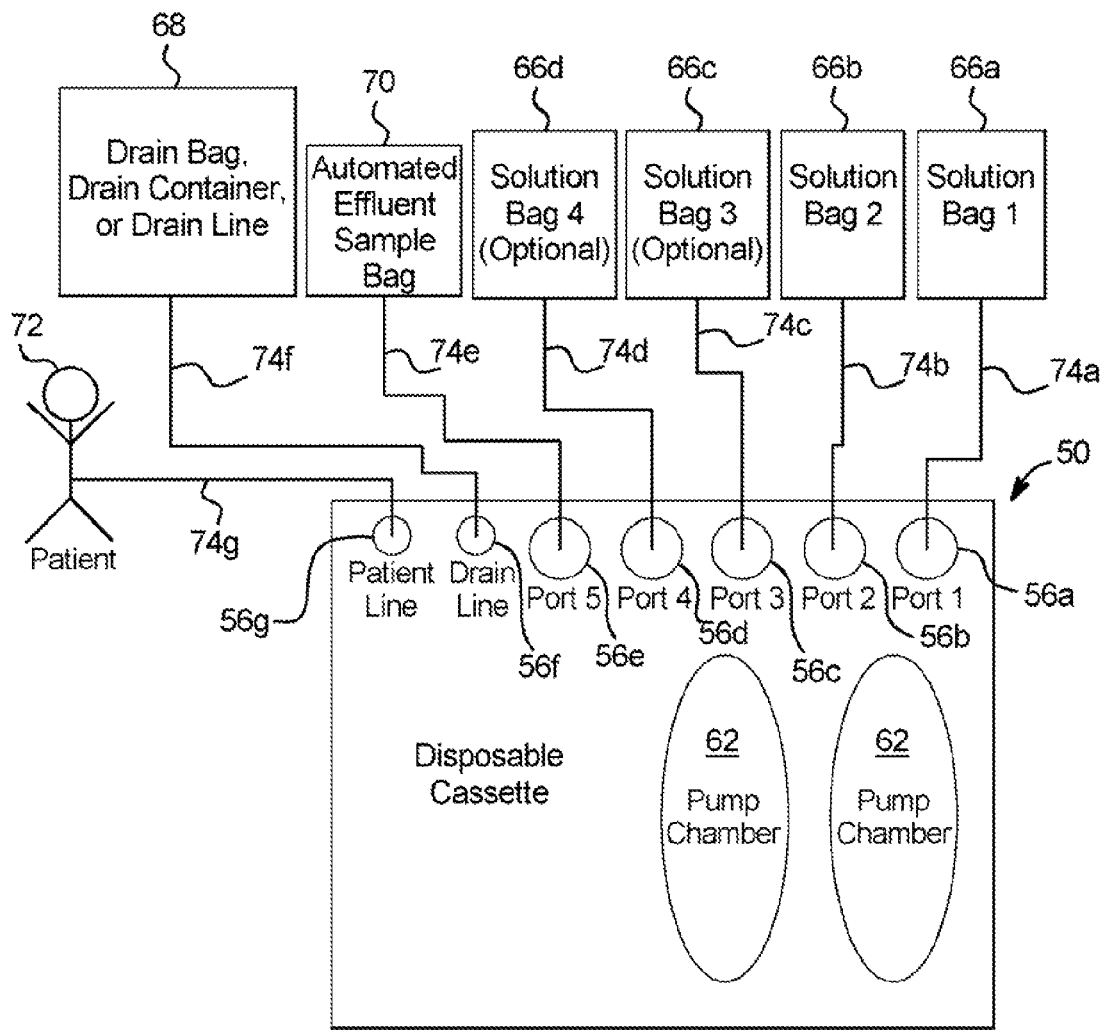
FIG. 3 is a schematic view of one embodiment of a disposable cassette and set used with the automated effluent sampling of the present disclosure.
Figure 4:
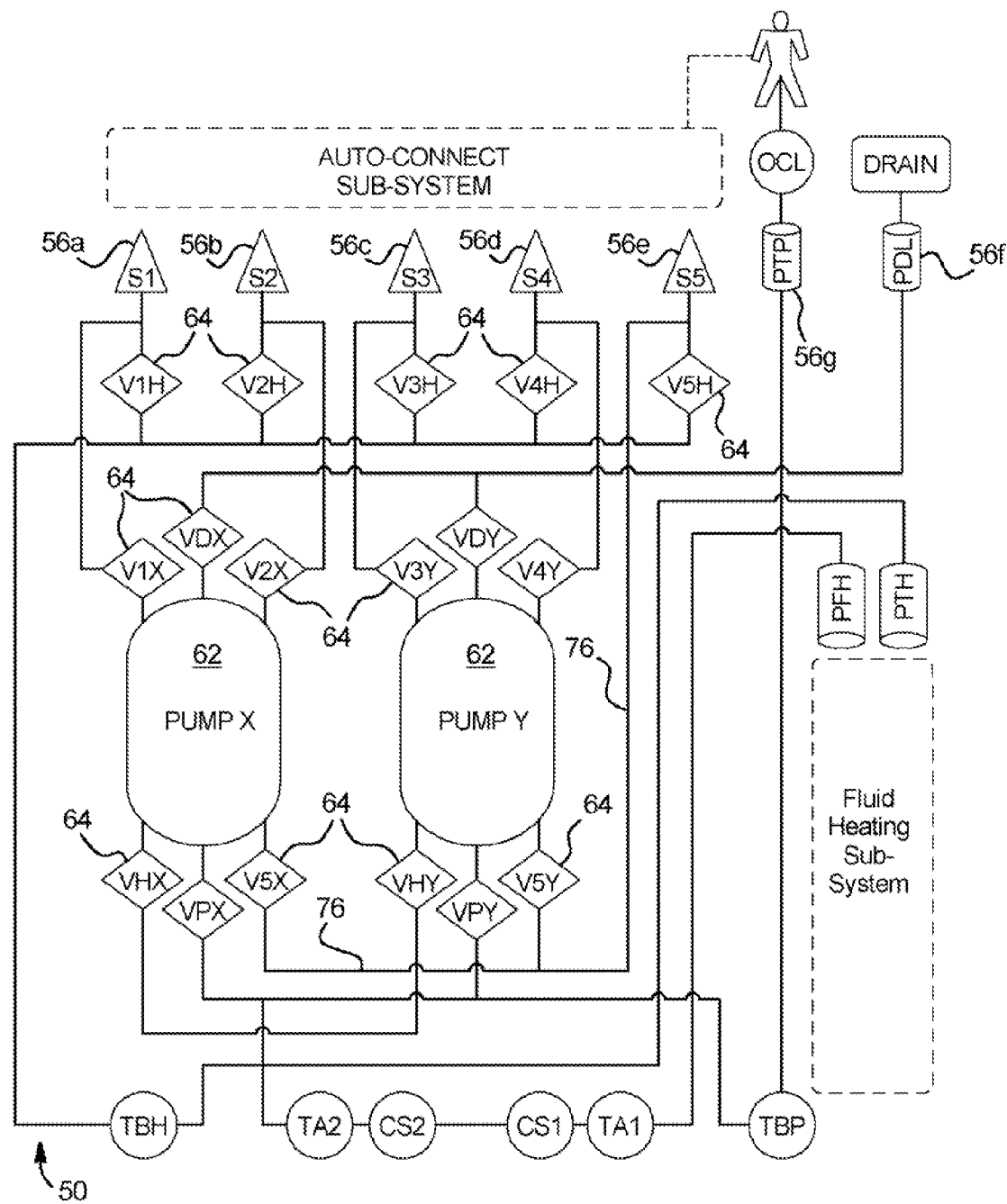
FIG. 4 is a schematic view of one embodiment of a pump chamber and valve chamber arrangement of the disposable cassette and set used with the automated effluent sampling of the present disclosure.
Figure 5:
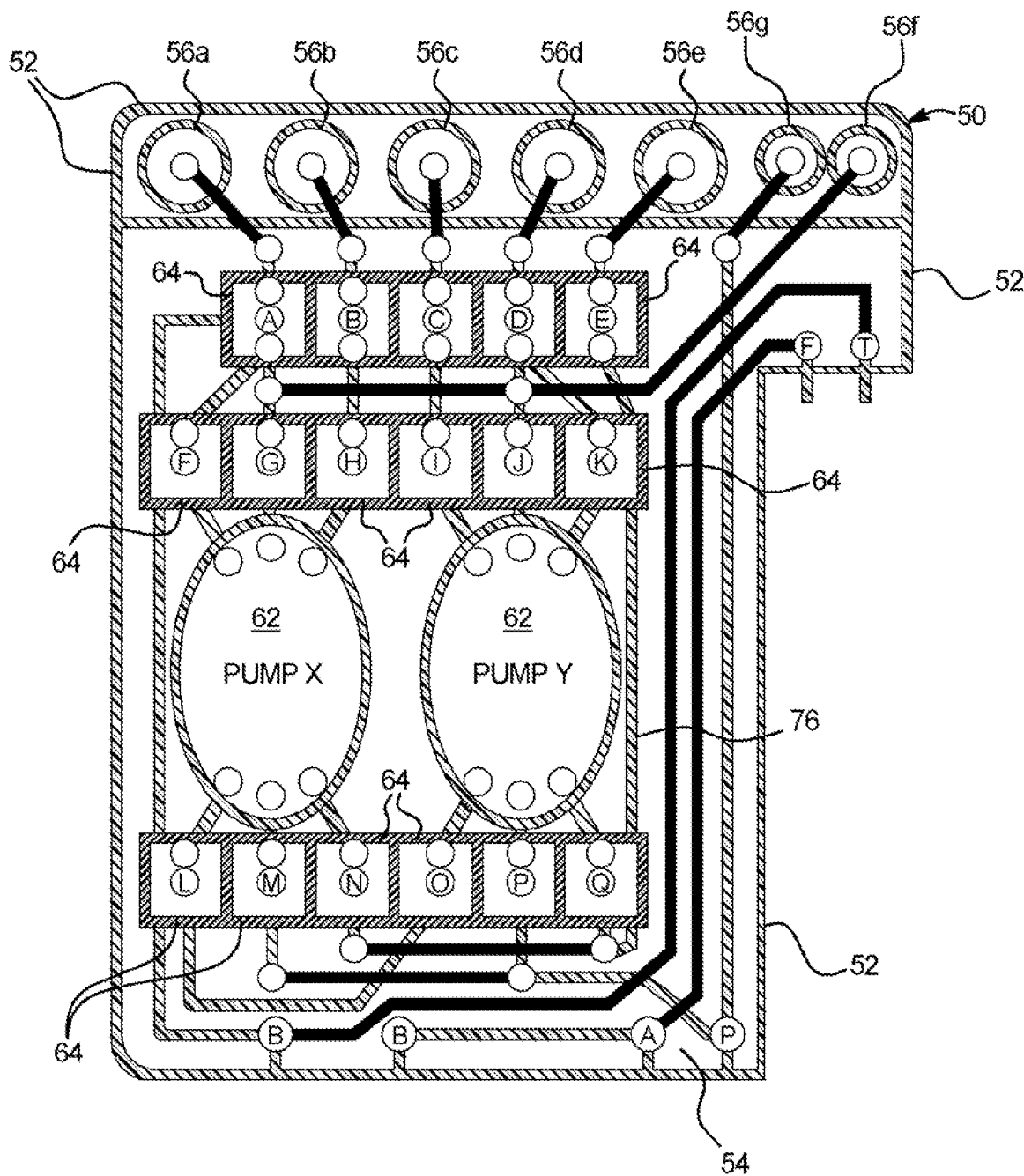
FIG. 5 is an elevation view of one embodiment of a pump chamber and valve chamber arrangement of the disposable cassette and set used with the automated effluent sampling of the present disclosure.

Referring now to FIGS. 3 to 5, cassette 50 is shown in various forms configured to operate with dialysis system 10 having an automated effluent sampling feature of the present disclosure. In particular, cassette 50 in FIG. 3 is shown connected operably to the patient and to various bags used in a dialysis treatment. FIG. 4 illustrates one embodiment for a flow schematic for cassette 50, which shows that both pumps can pump to the automated effluent sample bag shown in FIG. 3. FIG. 5 shows a physical cassette 50 including outer walls 52 and inner mid-plane or separation wall 54.

Cassette 50 in FIGS. 3 to 5 includes seven ports 56a to 56g and a pair of pump chambers 62. Cassette 50 alternatively includes a different number of ports and potentially only one pump chamber. Providing two pump chambers 62 and two associated pump instrument actuators allows the dialysis system to draw in fresh or spent dialysis fluid to one of the pump chambers 62, while simultaneously or virtually simultaneously pumping out of the second pump chamber 62 to the patient or drain, such that flow is at least substantially continuous. In the illustrated embodiment, ports 56a to 56d connect to supply or solution bags 66a to 66d. Port 56f is connected to a drain bag 68. Port 56g is connected fluidly to patient 72.

And as seen in FIG. 3, port 56e is connected fluidly to an automated effluent sample bag 70. One embodiment for automated effluent sample bag 70 and accompanying tubing is shown below in connection with FIG. 6. Each of the bags or containers 66a to 66d, 68 and 70 connects fluidly to ports 56a to 56f via a tube 74a to 74f, respectively. Likewise, patient 72 connects to patient line port 56g via tubing 74g.

As discussed above, in one embodiment tubing 74a to 74g is fixed to cassette 50 and includes a connector that connects to a mating connector at bag 66 (referring collectively to bags 66a to 66d or generally to one of those bags), bag 68 and bag 70. Alternatively, the tubing connectors connect to mating connectors, which in turn are connected to long-lines that extend from one of bags 66, 68 or 70. In a further alternative embodiment, each tubing 74a to 74g includes a connector that connects to ports 56a to 56g, respectively.

Cassette 50 of FIGS. 4 and 5 differs slightly from cassette 50 of FIG. 3 in that the end port of cassette 50 in FIGS. 4 and 5 is the drain port 56f, while the end port in cassette 50 of FIG. 3 is patient port 56g. It should be appreciated that the particular positions of ports 56a to 56g can be rearranged from the arrangements shown in FIGS. 3 to 5 based on fluid pathway placement and valve placement.

As is seen in FIGS. 4 and 5 effluent port 56e has a hydraulic pathway 76 to both pump chambers 62. Thus each pump chamber can pump to or from the effluent sample bag 70 in either the fill or drain mode. The effluent sampling uses effluent bag 70 and pump chambers 62 while in a drain mode, however, effluent sampling fluid can also be pulled from effluent bag 70. FIGS. 3 to 5 show that cassette 50 includes enough additional supply ports 56a to 56d to handle most types of PD therapies, while still allowing for the automated filling of effluent sample bag 70.

As seen in FIGS. 4 and 5, pump chamber Y can pump via valve V5Y, through effluent pathway 76, to port 56e and effluent bag 70, and vice versa. Valve V5Y in FIG. 4 corresponds to valve Q in FIG. 5. Pump chamber X can pump via valve V5X and effluent pathway 76 to port 56e and effluent bag 70, and vice versa. Valve V5X in FIG. 4 corresponds to valve N in FIG. 5.

As discussed above, when collecting a sample of the total effluent drain from the patient, dialysis instrument 12 in one embodiment ensures that the sample is representative of an entire drain volume by ratiometrically delivering most of the drain volume to drain bag 68 and a portion to effluent bag 70. For example, to obtain an approximate one liter sample of drain solution, given that a patient's total drain volume, including UF, is ten liters, instrument 12 first delivers nine pump-out strokes (e.g., alternating five pump-out strokes of pump chamber X and four pump-out strokes of pump chamber Y) to the drain bag and then delivers one pump-out stroke to effluent bag 70. In one sequence, only pump chamber Y (for example) pumps to effluent bag 70, e.g., on the tenth pump-out stroke. Alternatively, if the pump-out stroke to the effluent bag occurs on odd number (e.g., once every eleven strokes), both pump chambers X and Y are used to pump to effluent bag 70.

If it is desired that drain fluid be pumped from both pump chambers X and Y on an even pump-out stroke, it is possible to run a first sequence in which the first pump-out stroke is pumped to the effluent bag 70, after which the next nine pump-out strokes are pumped to drain bag 68. Next, a second sequence is run in which the first nine pump-out strokes are pumped to the drain bag 68, after which the final tenth pump-out stroke is pumped to effluent bag 70. Here, two pump-out strokes in a row from pump chambers X and Y are pumped to effluent bag 70. Alternatively, the alternating X and Y pump to effluent bag 70 strokes in an even stroke apportionment (e.g., once every ten pump strokes) are spaced apart by a number of pump strokes. For example, the first sequence can pump the fifth pump-out stroke from pump chamber X to effluent bag 70, while the second sequence can pump the fourth pump-out stroke from pump chamber Y to effluent bag 70.

As discussed above, when treatment is started, system 10 is primed with fresh dialysate. In one embodiment, during flushing and priming, ports 56a to 56d connected to solution bags 66a to 66d are primed and flushed to drain bag 68. Effluent sample bag 70 is not primed because it is flat (no solution, no air). When the patient is first drained, effluent comes from the patient, through line 74g and port 56g, into pump chambers 62 and out to drain bag 68 via port 56f and line 74f. When it is time to ratiometrically pump the first portion of the drain effluent for the sample, effluent is pushed though cassette pathway 76, port 56e and effluent line 74e (all of which contain sterile air, the air being pushed into the effluent sample bag 70) to effluent bag 70. The volumes of cassette effluent pathway 76 and effluent line 74e are known. To obtain the correct ratiometric volume of effluent fluid from each drain into sample bag 70, the instrument must correct for a volume that was used to displace the air in the lines during the first drain. To do this, for example, after the ratiometric portion of the last drain is pumped to the effluent sample bag 70, an additional volume of last drain effluent equal to the known volumes of pathway 76 and effluent line 74e is pumped to the sample bag 70.

Figure 6:
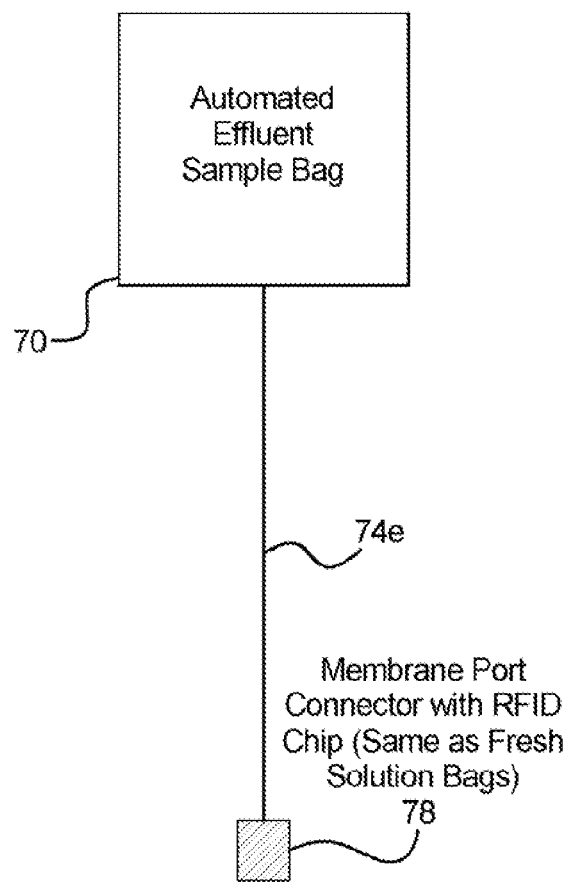
FIG. 6 is a plan view of one embodiment of an effluent sample bag used with the automated effluent sampling and peritoneal equilibration test ("PET") of the present disclosure.

Referring now to FIG. 6, one embodiment for automated effluent sample container 70 and effluent sample line 74e is illustrated. Bag 70 is sized to hold a desired sample. Bag 70 can be made of the same material as any of the supply or drain bags shown above. Likewise, effluent tubing 74e is an embodiment made of the same material as any of the other tubing lines 74 (referring collectively to any of tubing line 74a to 74g). In the illustrated embodiment, a connector 78 is placed at the end of tubing 74e. Connector 78 is configured to spike or be spiked by port 56e of cassette 50 in one embodiment. Connector 78 is fitted with an identification tag, such as a bar code or radio frequency identifier ("RFID") tag. One embodiment for tagged connector 78 is disclosed in connection with U.S. patent application Ser. No. 11/773,822, "Radio Frequency Auto-Identification System", filed Jul. 5, 2007, the entire contents of which are incorporated herein expressly by reference.

Connector 78 at the end of effluent line 74e mimics the configuration of the connectors placed at the ends of sample lines 74a to 74d, such that connector 78 spikes port 56e in the same manner as the connectors at the ends of any of solution lines 74a to 74d. This allows a fifth solution bag (for example) to be fitted to port 56e if needed and if the effluent sampling to bag 70 is not used.

The RFID or other type of identification tag allows for automatic touch-free connection and automatic machine recognition. Here, processing and software within instrument 12 recognizes that connector 78 is connected to an effluent sampling bag 70 and automatically recalls a program for use with an effluent sampling bag as opposed to a program for use with only supply bags. In an embodiment, the processing software also requests that the patient confirm that an effluent bag is to be used for a particular treatment, for example via an audio, visual or audiovisual message shown or provided at user interface 20.

Figure 7:
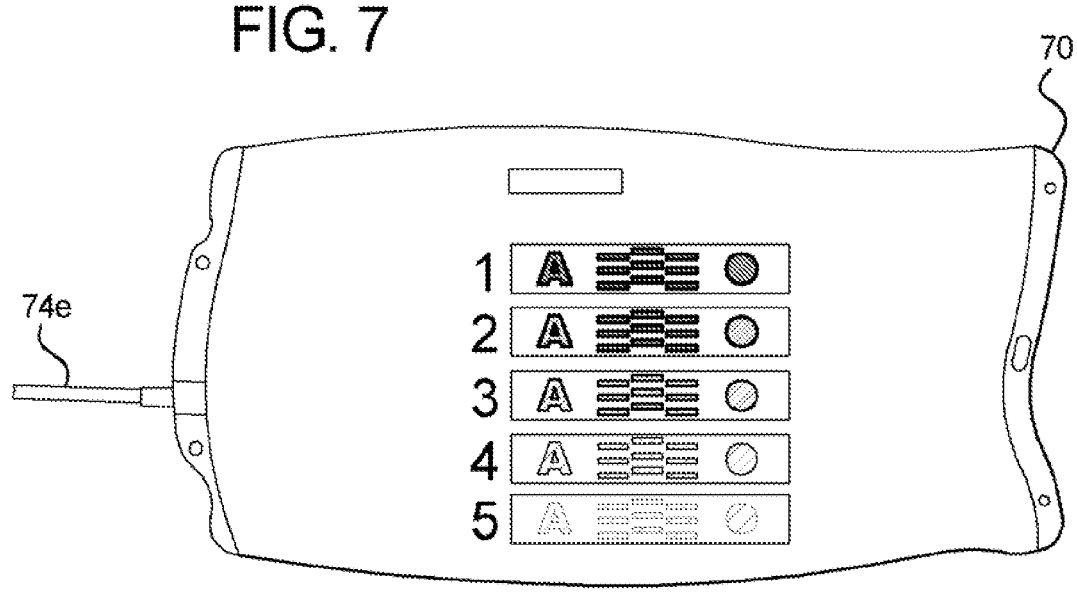
FIG. 7 is a plan view of another embodiment of an effluent sample bag used with the automated effluent sampling and PET of the present disclosure.

Referring now to FIG. 7, one embodiment for effluent sample bag 70 connected to tubing 74e is illustrated. Here, bag 70 is preprinted with five lines of text, illustrated in FIG. 7 as lines one to five. Each line of text becomes progressively lighter as illustrated. Instrument 12 instructs patients to determine how many lines of text are legible while looking through the bag with the printed text at the underneath side of the bag. That is, the patient has to look through the effluent sample to see how many lines of text one to five are visible. In an embodiment, the patient is instructed to place the bag 70 on a white or lighter colored table or support. The number of lines visible depends upon how cloudy the effluent sample is, which can help the patient to determine if the onset of peritonitis is likely. Bag 70 is shown illustrating Japanese characters, however, the text can be in any language or can be graphical shapes instead of actual text.

Automated Peritoneal Equilibration Test

Figure 8:
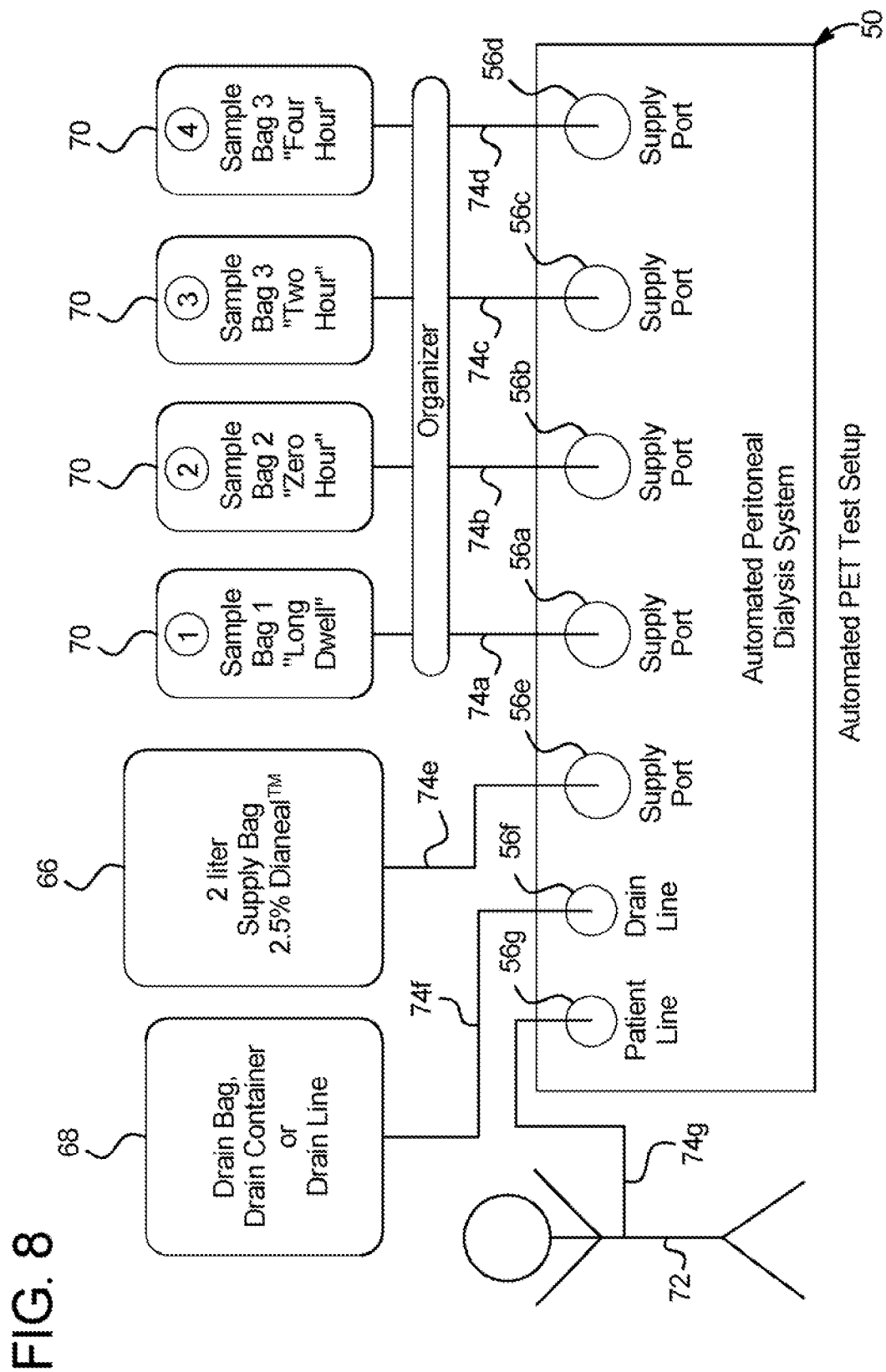
FIG. 8 is a schematic view of one embodiment of a disposable cassette and set used with the automated PET of the present disclosure.

Referring now to FIGS. 8 to 10, an automated system and method for performing a peritoneal equilibration test ("PET") is illustrated. FIGS. 3 to 7 illustrate a way to collect effluent in an single bag 70 automatically. Effluent bag 70 is useful for checking for an increase in cloudiness at the onset of peritonitis, for checking for a decrease in cloudiness when a known case of peritonitis is being treated and/or for taking an adequacy test sample to determine the effectiveness of a given prescription regime. The PET requires that multiple samples be taken and collected at different times. The PET provides a standard way to characterize a patient's peritoneal membrane transport characteristics. The PET indirectly determines how rapidly two small solutes (creatinine and glucose) are transported across the patient's peritoneal membrane. These results are compared to those from a large group of patients to categorize the patient's transport rate as high, high-average, low-average, or low.

The system and method of the PET of the present disclosure can be performed via instrument 12 discussed above. Further, cassette 50 including supply ports 56a to 56e, drain port 56f and drain port 56g and associated tubing can be used to perform system and method for PET that follows.

In the embodiment illustrated in FIG. 8, supply ports 56a to 56d are connected respectively to sample bags one to four via sample lines 74a to 74d, respectively. Additional supply ports 56 and sample bags 70 can be provided if needed. Supply port 56e is connected fluidly to supply bag 66 via supply line 74e. Port 56f is connected fluidly to drain bag 68 via tubing 74f. Port 56g is connected fluidly to the patient 72 via tubing 74g. Tubing 74 (tubes 74a to 74f) can include connectors that connect to ports 56a to 56g, respectively. Alternatively, tubing 74 is connected to ports 56 (ports 56a to 56g) permanently and is attached to bags 66, 68 and 70 via connectors on the bags or long-lines extending from the bags. Line 74g in one embodiment extends from patient port 56g to patient 72 and can for example be ten feet long.

Any of the embodiments for identifying connectors that connect to ports 56 discussed above are applicable to the automated PET system and method shown in connection with FIGS. 8 to 10. For example, the smart system can determine whether port 56e is connected to a standard supply bag 66, an effluent sample bag 70 shown in connection with FIGS. 3 to 7 or a supply bag 66 dedicated to the automated PET shown in connection with FIG. 8. Likewise, the auto-identification mechanism of system 10 can determine for ports 56a to 56d whether a supply bag 66 is connected to those ports or whether a sample bag 70, such as sample bags one to four, respectively, as shown in FIG. 8 is connected to one of ports 56a to 56d. The processing and memory are configured to know when the particular bag combination of FIG. 8 is installed into cassette 50. Again one suitable system for such detection is set forth in the application referenced above. Alternatively, the patient or caregiver informs the machine 10 that the cassette has been connected to a PET sampling disposable. In either case, instrument 12 runs one of the automated PET's discussed next in connection with FIGS. 9 and 10.

Referring now to FIG. 9, which includes FIGS. 9A and 9B, sequence 100 illustrates one possible automated PET that the above-described instrument 12 and disposable apparatus 50 can perform. Upon beginning sequence 100 as shown in connection with oval 102, the patient in the evening begins an eight to twelve hour long dwell after having filled with a full, e.g., two liters of 2.5 percent dextrose PD solution, as seen at block 104. One suitable 2.5 percent dextrose solution is marketed as Dianeal™ solution provided by the assignee of the present disclosure.

At block 106, in the morning after completion of the eight to twelve hour long dwell of block 104, the patient or caregiver (i) loads a new disposable set of FIG. 8, including a cassette 50, (ii) connects a two (or 2.5) liter supply bag 66 of, e.g., 2.5 percent dextrose PD solution connected to port 56e of cassette 50, and (iii) connects four, e.g., 200 ml, sample bags 70 as seen in FIG. 8. System 10 prompts the patient or caregiver to mark each sample bag 70 with indelible pen, e.g.: "long dwell", "zero-hour", "two-hour", and "four-hour". Alternatively, bags 70 are preprinted each with one of such markings or with each marking and a check box next to each marking. Further alternatively, the four bags are provided as a set of pre-marked bags, with the bag connectors held in a specific order by an organizer that requires loading in the same order so that system 10 knows which bag is connected to which cassette port. Still further alternatively, bags 70 are supplied pre-marked with one of the four sample types and an identification tag that matches the marking.

The patient connects himself/herself to the disposable set. Sequence 100 in one embodiment expects that the patient will have a line 74g to cassette 50 of about ten feet and that the pump chambers will retain a residual volume of fluid. Sequence 100 compensates accordingly for both those volumes.

At block 108, system 10 using the automated PET apparatus of FIG. 8 performs a long dwell sample in which instrument 12 prompts patient 72 to sit up and drains the patient via the drain line 74f and drain bag 68 (using both pump chambers). After fully flushing fluid to the disposable set with effluent to drain line 74f, system 10 diverts approx 200 ml of the drain volume to the long dwell sample bag (e.g., sample bag 1 in FIG. 8). Such procedure can consume about twenty minutes. Instrument 12 records the following: (i) fill volume and concentration of long dwell solution; (ii) the actual duration of the previous long dwell; (iii) the actual duration of the current drain; and (iv) the total volume drained.

At block 110, instrument 12 prompts the patient to assume a supine position (lying down with the face up). Instrument 12 delivers, e.g., 2010 ml of 2.5% percent dextrose solution in, e.g., ten minutes. After the infusion of each 400 ml, instrument 12 prompts the patient to roll from side to side to ensure uniform distribution of the solution within the patient's peritoneum. Instrument 12 records the following: (i) actual time to perform the fill; and (ii) the clock time of the end of the fill, which is set to the zero hour dwell time for use at block 112.

At block 112, system 10 records the zero hour sample. At the end of the fill of block 110, instrument 12 drains approximately forty ml (volume of the patient line) to drain line 74f to flush the patient line 74g using one of the pump chambers 62 (e.g., chamber X). Instrument 12 then drains 200 ml of the fluid that was just infused to the patient into the sample bag labeled zero-hour dwell or sample bag (e.g., sample bag 2 in FIG. 8), using the other pump chamber 62 (chamber Y). Instrument 12 then pulls 190 ml from the zero-hour sample bag 70 and pumps the 190 ml to patient 72 via second pump chamber Y, leaving a 10 ml sample in zero-hour dwell bag 70 (sample bag 2 in FIG. 8). Instrument 12 then pumps forty ml of fresh dialysate from supply bag 66 to patient 72 via first pump chamber X. This fresh solution only flows through patient line 74g, pushing the solution in that line back to the patient. The Patient 72 can then disconnect from instrument 12 or remain connected until the next sample.

At block 114, system 10 performs a two hour effluent sample and a two hour blood sample used for PET. The solution filled at block 110 continues to dwell in the patient's peritoneum until two hours after the zero-hour dwell time. Patient 72 if disconnected reconnects to instrument 12 prior to the end of the two hours. At the end of two hours, instrument 12 drains approximately forty ml (volume of the patient line) to drain line 74f to flush the patient line 74g using one of the pump chambers 62 (e.g., chamber X). Instrument 12 then drains two-hundred ml of effluent from patient 72 into sample bag 170 marked two-hour dwell (e.g., sample bag 3 in FIG. 8) using pump chamber Y. Instrument 12 then pulls 190 ml from the two-hour sample bag 70 and pumps the 190 ml to patient 72 via second pump chamber Y, leaving a 10 ml sample in two-hour dwell bag 70 (sample bag 3 in FIG. 8). Instrument 12 then pumps forty ml of fresh dialysate from supply bag 66 to patient 72 via first pump chamber X. This fresh solution only flows through patient line 74g, pushing the solution in that line back to the patient. Instrument 12 records the time of sample. Also, at this time, patient 72, a nurse or a clinician takes a two-hour blood sample from the patient.

At block 116, the solution of the fill of block 110 is allowed to continue to dwell in the peritoneum until four hours after the zero-hour dwell time. Patient 72 if disconnected from instrument 12 reconnects to the instrument prior to the end of the four hours. At the end of the 4 hours, instrument 12 prompts patient 72 to assume a sitting position and begins to drain effluent from patient 72 to drain line 74f and drain bag 68 using both pump chambers X and Y. After fully flushing fluid to the disposable set with effluent to drain line 74f, instrument 12 diverts approximately 200 ml of the drain volume to the sample bag 70 marked four-hour dwell (e.g., sample bag 4 in FIG. 8) and completes the drain to drain line 74f and drain bag 68 (approximately twenty minutes). Instrument 12 records the following: (i) time of sample; and (ii) the total drained volume.

The four PET samples concludes sequence 100, so that patient 72 can disconnect from instrument 12, after which the PET ends as seen at oval 118.

Referring now to FIG. 10, which includes FIGS. 10A, 10B and 10C, sequence 200 illustrates another possible automated PET (modified PET) contemplated for the above-described instrument 12 and disposable apparatus 50. The disposable set including cassette 50 for sequence 200 can be the same as for sequence 100 except that a two liter supply bag 66 (for example) for sequence 100 is replaced with a larger supply bag (e.g., 2.5 liter) for sequence 200. The larger supply bag 66 for sequence 200 doubles as the four hour supply bag. Here too, bag 3 becomes the one hour dwell bag and bag 4 becomes the two hour dwell bag.

Upon beginning sequence 200 as shown in connection with oval 202, the patient in the evening begins an eight to twelve hour long dwell after having filled with a full, e.g., two liters of 2.5 percent dextrose PD solution, as seen at block 204. One suitable 2.5 percent dextrose solution is marketed as Dianeal™ solution provided by the assignee of the present disclosure.

At block 206, in the morning after completion of the eight to twelve hour long dwell of block 204, the patient or caregiver (i) loads a new disposable set of FIG. 8, including a cassette 50, (ii) connects a 2.5 liter (for example) supply bag 66 of, e.g., 2.5 percent dextrose PD solution to port 56e of cassette 50, and (iii) connects four, e.g., 200 ml sample bags 70 as seen in FIG. 8. System 10 prompts the patient or caregiver to mark each sample bag 70 with indelible pen, e.g.: "long dwell", "zero-hour", "one-hour", "two-hour", and "four-hour". The four-hour sample will be taken in the emptied supply bag 66, allowing five samples to be taken with only five ports, in which one port (56e in FIG. 8) is also used to connect to supply fluid 66. Alternatively, bags 70 come preprinted with one of such markings or with each marking and a check box next to each marking or according to any of the embodiments discussed above for sequence 100.

At block 208, system 10 using the automated PET apparatus of FIG. 8 performs a long dwell sample in which instrument 12 prompts the patient to sit-up and drains patient 72 to the drain line 74f and drain bag 68 using both pump chambers X and Y. The instrument 12 diverts approx 200 ml of the drain volume to the long dwell sample bag (e.g., sample bag 1 in FIG. 8). Such procedure can consume about twenty minutes. Instrument 12 records the following: (i) fill volume and concentration of long dwell solution; (ii) the actual duration of the previous long dwell; (iii) the actual duration of the current drain; and (iv) the total volume drained.

At block 210, instrument 12 prompts the patient to assume a supine position (lying down with the face up). Instrument 12 delivers, e.g., 2010 ml of 2.5% percent dextrose solution in, e.g., ten minutes. After the infusion of each 400 ml, instrument 12 prompts the patient to roll from side to side to ensure uniform distribution of the solution within the patient's peritoneum. Instrument 12 records the following: (i) actual time to perform the fill; and (ii) the clock time of the end of the fill, which is set to the zero hour dwell time for use at block 212.

At block 212, system 10 records the zero hour sample. At the end of the fill of block 210, instrument 12 drains approximately forty ml (volume of the patient line) to drain line 74f to flush the patient line 74g using one of the pump chambers 62 (e.g., chamber X). Instrument 12 then drains 200 ml of the fluid that was just infused to the patient into the sample bag labeled zero-hour dwell or sample bag (e.g., sample bag 2 in FIG. 8), using the other pump chamber 62 (chamber Y). Instrument 12 then pulls 190 ml from the zero-hour sample bag 70 and pumps the 190 ml to patient 72 via second pump chamber Y, leaving a 10 ml sample in zero-hour dwell bag 70 (sample bag 2 in FIG. 8). Instrument 12 then pumps forty ml of fresh dialysate from supply bag 66 to patient 72 via first pump chamber X. This fresh solution only flows through patient line 74g, pushing the solution in that line back to the patient. The Patient 72 can then disconnect from instrument 12 or remain connected until the next sample.

At block 214, system 10 performs a one hour effluent sample. The solution filled at block 210 continues to dwell in the patient's peritoneum until one hour after zero-hour dwell time. Patient 72 if disconnected reconnects to instrument 12 prior to the end of the one hour. At the end of one hour, instrument 12 drains approximately forty ml (volume of the patient line) to drain line 74f to flush the patient line 74g using one of the pump chambers 62 (e.g., chamber X). Instrument 12 then drains two-hundred ml of effluent from patient 72 into sample bag 170 marked one-hour dwell (e.g., sample bag 3 in FIG. 8 but which is now marked "one hour") using pump chamber Y. Instrument 12 then pulls 190 ml from the one-hour sample bag 70 and pumps the 190 ml to patient 72 via second pump chamber Y, leaving a 10 ml sample in one-hour dwell bag 70 (sample bag 3 in FIG. 8). Instrument 12 then pumps forty ml of fresh dialysate from supply bag 66 to patient 72 via first pump chamber X. This fresh solution only flows through patient line 74g, pushing the solution in that line back to the patient. Instrument 12 records the time of sample.

At block 216, system 10 performs a two hour effluent sample and a two hour blood sample used for PET. The solution filled at block 210 continues to dwell in the patient's peritoneum until two hours after zero-hour dwell time. Patient 72 if disconnected reconnects to instrument 12 prior to the end of the two hours. At the end of two hours, instrument 12 drains approximately forty ml (volume of the patient line) to drain line 74f to flush the patient line 74g using one of the pump chambers 62 (e.g., chamber X). Instrument 12 then drains two-hundred ml of effluent from patient 72 into sample bag 170 marked two-hour dwell (e.g., sample bag 4 in FIG. 8 but which is now marked "two hour") using pump chamber Y. Instrument 12 then pulls 190 ml from the two-hour sample bag 70 and pumps the 190 ml to patient 72 via second pump chamber Y, leaving a 10 ml sample in two-hour dwell bag 70 (sample bag 4 in FIG. 8). Instrument 12 then pumps forty ml of fresh dialysate from supply bag 66 to patient 72 via first pump chamber X. This fresh solution only flows through patient line 74g, pushing the solution in that line back to the patient. Instrument 12 records the time of sample. Also, at this time, patient 72, a nurse or a clinician takes a two-hour blood sample from the patient.

Prior to the last sample, any remaining solution in the, e.g., 2.5 liter supply bag 66 is emptied to drain line 68. The patient for example may only have filled two (or a little more) from a 2.5 liter supply bag for example, leaving residual supply fluid in the supply bag 66. Supply bag 66 should be emptied so it can be used as a fifth sample bag. Patient may now disconnect or remain connected until the last sample.

At block 218, the solution of the fill of block 110 is allowed to continue to dwell in the peritoneum until four hours after the zero-hour dwell time. Patient 72 if disconnected from instrument 12 reconnects to the instrument prior to the end of the four hours. At the end of the 4 hours, instrument 12 prompts patient 72 to assume a sitting position and begins to drain effluent from patient 72 to drain line 74f and drain bag 68 using both pump chambers X and Y. After fully flushing fluid to the disposable set with effluent to drain line 74f, instrument 12 sequentially diverts approximately 500 ml of the drain volume to the sample bag marked four-hour dwell (e.g., emptied supply bag 66 in FIG. 8) and then pumps that 500 ml to drain line 74f and drain bag 68. Instrument 12 repreates this process three more times to remove the approximate 2000 ml of fluid from patient 72. In the last cycle, instrument 12 leaves a small sample (e.g., ten to 30 ml) in supply bag 66/four hour sample bag. The sample alternatively is taken via a syringe so that the larger supply bag does not have to be transported for testing. Instrument 12 records the following: (i) time of sample; and (ii) the total drained volume.

The five PET samples concludes sequence 200, so that patient 72 can disconnect from instrument 12, after which the PET ends as seen at oval 220.

When supply bag 66 doubles as one of the sample bags as in sequence 200, it is possible that not all of the fresh solution is removed from the supply bag before it is filled with the effluent sample. Sequence 200 accordingly pumps 500 ml of solution to the supply bag/sample bag and then empties the supply bag/sample bag to the drain line. Performing such operation a total of four times is possible with a 2000 ml fill volume. Thus, if as much as 100 ml is left behind in supply bag/sample bag on each successive dilution (extreme case), the present method effectively reduces the dilution error to an insignificant level as shown: 100/600*100/600*100/600*100/600=0.00077. The effluent in the supply bag would be in the example at 99.92% of the concentration, which would have been present had a completely empty bag been used for sampling. Thus while supply bag 66 could alternatively be any of the "zero hour", "one hour" or "two hour" sample bags, these bags would not allow for the above dilution.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis system comprising:
   at least one dialysis fluid pump actuator;
   a drain line, a sample container and a solution container;
   a disposable cassette connected to the drain line, the sample container and the solution container, and including at least one pump chamber operable with the at least one pump actuator to pump fluid to and from the sample container, the disposable cassette further including a plurality of fluid ports configured to be connected fluidly to a plurality of fluid containers; and
   a processor programmed to cause the at least one pump actuator to operate the at least one pumping chamber to collect an effluent dialysis fluid sample by (i) selectively moving effluent dialysis fluid to the sample container and (ii) returning a portion of the effluent dialysis fluid from the sample container to the patient, the remainder of the effluent dialysis fluid in the sample container forming the sample.

2. The dialysis system of claim 1, wherein the sample container is printed with indicia having decreasing darkness for evaluation of the effluent dialysis fluid stored in the sample container.

3. The dialysis system of claim 1, including at least one valve actuator operable with at least one valve chamber of the disposable cassette, the processor further programmed to cause the at least one valve actuator to operate the at least one valve chamber to selectively move effluent dialysis fluid to the sample container.

4. The dialysis system of claim 1, which includes a sensor configured to sense an identifier associated with the sample container when connected to the disposable cassette.

5. The dialysis system of claim 4, the sensor further configured to sense an identifier associated with a supply container when the supply container is connected to the disposable cassette instead of the sample container.

6. The dialysis system of claim 5, the processor further configured to cause the at least one pump actuator to operate the at least one pump chamber to move effluent dialysis fluid to the drain line only when the supply container is connected to the disposable cassette instead of the sample container.

7. The dialysis system of claim 1, which includes a user interface programmed to provide at least one of (i) an operator input that the sample container is being used; (ii) output instructions regarding use of the sample container via voice guidance; and (iii) output instructions regarding use of the sample container via graphics.

8. The dialysis system of claim 1, the disposable cassette including a drain port and a plurality of supply ports, at least one of the supply ports configured to operate alternatively as a sample port.

9. The dialysis system of claim 8, the drain port and the at least one sample port each in valved communication with a plurality of the pump chambers.

10. The dialysis system of claim 1, the processor programmed to cause the at least one pump actuator to operate with the at least one pump chamber to pump a first number of pump strokes to the drain line followed by a second number of pump strokes to the sample container.

11. A dialysis fluid system comprising:
    at least one dialysis fluid pump actuator;
    a drain line, a first sample container, a second sample container and a solution container;
    a disposable cassette connected to the drain line, the first sample container, the second sample container and the solution container, and including at least one pump chamber operable with the at least one pump actuator to pump fluid (i) from the patient to the first sample container and the second sample container, and (ii) from the first sample container and the second sample container to the patient, the disposable cassette further including a plurality of fluid ports configured to be connected fluidly to a plurality of fluid containers; and
    a processor programmed to cause the at least one pump actuator to operate the at least one pump chamber to collect a plurality of effluent dialysis fluid samples by pumping (i) a first sample of effluent dialysis fluid from a patient to the first sample container at a first time and (ii) a second sample of effluent dialysis fluid from the patient to the second sample container at a second time.

12. The dialysis fluid system of claim 11, wherein the first time is prior to a patient fill and the second time is directly after the patient fill.

13. The dialysis fluid system of claim 11, the processor further programmed to cause the at least one pump actuator to operate the at least one pump chamber to pump a third sample of effluent dialysis fluid to a third sample container at a third time.

14. The dialysis fluid system of claim 13, wherein the third time is one of one hour and two hours from an end of a patient fill.

15. The dialysis fluid system of claim 13, the processor further programmed to cause the at least one pump actuator to operate the at least one pump chamber to pump a fourth sample of effluent dialysis fluid to a fourth sample container at a fourth time.

16. The dialysis fluid system of claim 15, wherein the fourth time is one of two hours and four hours from an end of a patient fill.

17. The dialysis fluid system of claim 15, which is configured to prompt a blood test of the patient at one of the third and fourth times.

18. The dialysis fluid system of claim 15, wherein the processor is programmed such that more than a sample volume's worth of effluent dialysis fluid is pumped to at least one of the third and fourth sample containers, and effluent dialysis fluid is thereafter removed from the respective sample container until a desired sample volume remains in the container.

19. The dialysis fluid system of claim 18, the processor still further programmed to return the removed effluent dialysis fluid to the patient.

20. The dialysis fluid system of claim 15, the processor further programmed to clear a patient line by pumping a patient line volume's worth of fluid from the patient line to a drain/drain container before pumping at least one of (i) the third sample of effluent dialysis fluid from the patient to the third sample container and (ii) the fourth sample of effluent dialysis fluid from the patient to the fourth sample container.

21. The dialysis fluid system of claim 15, the processor further programmed to cause the at least one pump actuator to operate the at least one pump chamber to pump a fifth sample of effluent dialysis fluid to a fifth sample container at a fifth time.

22. The dialysis fluid system of claim 21, wherein the fifth sample container is an emptied supply container.

23. The dialysis fluid system of claim 11, wherein the first sample of effluent dialysis fluid is from a total drain of the patient after a long dwell within the patient.

24. The dialysis fluid system of claim 11, wherein the processor is programmed such that more than a sample volume's worth of effluent dialysis fluid is pumped to at least one of the first and second sample containers and effluent dialysis fluid is thereafter removed from the respective sample container until a desired sample volume remains in the container.

25. The dialysis fluid system of claim 24, the processor still further programmed to return the removed effluent dialysis fluid to the patient.

26. The dialysis fluid system of claim 11, the processor further programmed to clear a patient line by pumping a patient line volume's worth of fluid from the patient line to a drain/drain container before pumping at least one of (i) the first sample of effluent dialysis fluid from the patient to the first sample container and (ii) the second sample of effluent dialysis fluid from the patient to the second sample container.

27. The dialysis fluid system of claim 11, which is operated via at least one of voice guidance and a graphical user interface.

28. A dialysis fluid system comprising:
at least one dialysis fluid pump actuator;
a drain line, a first sample container, a second sample container and a solution container;
a disposable cassette connected to the drain line, the first sample container, the second sample container and the solution container and including at least one pump chamber operable with the at least one pump actuator to pump fluid to and from the first sample container and the second sample container, the disposable cassette further including a plurality of fluid ports configured to be connected fluidly to a plurality of fluid containers; and
a processor programmed to cause the at least one pump actuator to operate the at least one pump chamber to collect a plurality of effluent dialysis fluid samples by pumping (i) a first sample of effluent dialysis fluid from a patient to the first sample container at a first time, (ii) a second sample of effluent dialysis fluid from the patient to the second sample container at a second time and (iii) a portion of effluent dialysis fluid from the first sample container to the patient, the second sample container to the patient, or both sample containers to the patient.

* * * * *